(12) United States Patent
Ball (10) Patent No.: US 7,877,275 B2
(45) Date of Patent: Jan. 25, 2011

(54) SYSTEM AND METHOD FOR MAINTAINING AND PROVIDING PERSONAL INFORMATION IN REAL TIME

(75) Inventor: William L. Ball, Grosse Pointe Farms, MI (US)

(73) Assignee: General Motors LLC, Detroit, MI (US)

( * ) Notice: Subject to any disclaimer, the term of this patent is extended or adjusted under 35 U.S.C. 154(b) by 1583 days.

(21) Appl. No.: 10/712,480

(22) Filed: Nov. 13, 2003

(65) Prior Publication Data

US 2005/0107673 A1    May 19, 2005

(51) Int. Cl.
*G06F 19/00* (2006.01)

(52) U.S. Cl. .................... 705/3; 705/2; 600/300

(58) Field of Classification Search ............... 705/2, 705/26, 3; 600/300, 301, 504, 509; 455/404.2, 455/404, 404.1; 370/328, 329; 701/1, 211; 340/573.4, 988, 539.12; 307/10.5; 702/183; 348/148; 709/250, 217, 203
See application file for complete search history.

(56) References Cited

U.S. PATENT DOCUMENTS

| | | | | |
|---|---|---|---|---|
| 5,652,570 A | * | 7/1997 | Lepkofker | 340/573.4 |
| 5,949,152 A | * | 9/1999 | Tagawa et al. | 307/10.5 |
| 6,028,537 A | * | 2/2000 | Suman et al. | 340/988 |
| 6,524,239 B1 | * | 2/2003 | Reed et al. | 600/300 |
| 6,526,335 B1 | * | 2/2003 | Treyz et al. | 701/1 |
| 6,579,231 B1 | * | 6/2003 | Phipps | 600/300 |
| 6,642,855 B2 | | 11/2003 | Budnovitch | 340/932.2 |
| 6,757,262 B1 | * | 6/2004 | Weisshaar et al. | 370/310 |
| 7,068,993 B2 | * | 6/2006 | Rai et al. | 455/404.1 |
| 7,099,835 B2 | * | 8/2006 | Williams, III | 705/26 |
| 2001/0026240 A1 | * | 10/2001 | Neher | 342/357.07 |
| 2001/0034223 A1 | * | 10/2001 | Rieser et al. | 455/404 |
| 2002/0003571 A1 | * | 1/2002 | Schofield et al. | 348/148 |
| 2002/0049535 A1 | * | 4/2002 | Rigo et al. | 701/211 |
| 2002/0063637 A1 | * | 5/2002 | Eida et al. | 340/901 |
| 2002/0103622 A1 | * | 8/2002 | Burge | 702/183 |
| 2003/0109245 A1 | * | 6/2003 | McCalmont et al. | 455/404 |
| 2003/0231550 A1 | * | 12/2003 | Macfarlane | 367/198 |
| 2004/0130446 A1 | * | 7/2004 | Chen et al. | 340/539.12 |
| 2005/0153681 A1 | * | 7/2005 | Hanson | 455/404.2 |
| 2005/0250468 A1 | * | 11/2005 | Lu et al. | 455/403 |

OTHER PUBLICATIONS

Birch, S., Car with eyes and ears takes a look into the future. [Final 1 Edition] The Times. London (UK): Dec. 8, 2001. p. 44. [Retrieved from Internet Aug. 31, 2008] URL: <http://proquest.umi.com/pqdweb?did=93994591&sid=12&Fmt=3&clientId=19649&RQT=309&VName=PQD>.*

(Continued)

*Primary Examiner*—Gerald J. O'Connor
*Assistant Examiner*—Natalie A Pass
(74) *Attorney, Agent, or Firm*—Dierker & Associates, P.C.

(57) ABSTRACT

The invention provides a method and system for communicating a vehicle user's medical information stored in a key device to medical caregivers via a wireless communications network. The method comprises receiving vehicle user medical information in a key device, transmitting the medical information from the key device to a storage unit within a vehicle and transmitting the stored medical information from a telematics unit to a call center responsive to an emergency event.

15 Claims, 4 Drawing Sheets

OTHER PUBLICATIONS

The new Volvo concept car reaps the benefits of Fingerprint Card technology. 2001. [Retrieved on Mar. 11, 2009]. Retrieved from Internet.URL: <http://www.fingerprints.com/Investor%20relations/News%20and%20Events/2001/The%20new%20Volvo%20concept%20car%20reaps%20the%20benefits%20of%20Fingerprint%20Ca rd%20technology.aspx>.*

Volvo Personal Communicator. 2001. [Retrieved on Mar. 10, 2009]. Retrieved from Internet.URL: <http://www.fingerprints.com/Investor%20relations/News%20and%20Events/2001/Volvo%20Personal%20Communicator.aspx>.*

Press Release: Roadside Telematics Corp. Selects Kivera as Location-Based Services Partner; Kivera and Roadside Offer First Location-Based, Emergency Response Solution to Customers. 2001. [Retrieved on Mar. 15, 2009]. Retrieved from Internet.URL: <http://www.directionsmag.com/press.releases/index.php?duty=Show&id=4133&trv=1>.*

Royal Ford. (Mar. 17, 2000). Telematics will keep you in touch: Your wired car can summon help when you can't :[Final Edition]. Edmonton Journal,p. H8. Retrieved Aug. 9, 2009, from Canadian Newsstand Complete. (Document ID: 220681141).*

Dave Boe. (Nov. 16, 1998). OnStar links up with Naperville medical information firm:[Lake Edition]. Daily Herald, p. 1 Retrieved Aug. 9, 2009, from ProQuest Newsstand. (Document ID: 36037256).*

Royal Ford, Globe Staff. (Mar. 4, 2000). Telematics: Interactive System Is the Next Word in Communication :[Third Edition]. Boston Globe,p. D.1. Retrieved Aug. 9, 2009, from Business Dateline. (Document ID: 50786088).*

Volvo Cars of North America Unveils Their First Telematics System for 2003 Models. (Oct. 7). PR Newswire,1. Retrieved Aug. 9, 2009, from Business Dateline. (Document ID: 205668491).*

* cited by examiner

SYSTEM AND METHOD FOR MAINTAINING AND PROVIDING PERSONAL INFORMATION IN REAL TIME

FIELD OF THE INVENTION

This invention relates generally to data transmissions over a wireless communication system. More specifically, the invention relates to a key system that includes a personalized key device for storing and transmitting personal information.

BACKGROUND OF THE INVENTION

Wireless communication services for mobile vehicles, such as navigation and roadside assistance, have increased rapidly in recent years and are expanding into new service areas. One such new area of service involves summoning emergency response teams to the site of a service subscriber's vehicle after the vehicle has been involved in an accident. The request for emergency assistance may be sent via a vehicle occupant or, under some circumstances, may be sent by the vehicle.

Emergency situations that involve medical assistance often require personal medical information about the person that is being treated. However, medical history information is not always available at the site of a traffic accident for the person requiring treatment. This may be due to, for example, the patient being unable to communicate.

One current system of alerting emergency medical professionals that a patient has special medical needs requires that the patient wear a bracelet or necklace bearing an emblem, for example, a MedicAlert® bracelet. The bracelet or necklace may include an engraved telephone number and medical information. For example, the bracelet may include information indicating that the patient is diabetic, allergic to certain medications or has surgical implants, such as a stent or a pacemaker. The telephone number that may be included on the bracelet can be used to contact a third party having additional information regarding the patient.

Though medical alert bracelets may provide needed information and peace of mind for the wearer, they do have serious limitations. One such limitation is the size of the engraving surface of the jewelry. In order to remain both wearable and fashionable, the size of the jewelry is kept small. Consequently, the size of the bracelet or necklace does not always allow a complete medical history to be engraved on the surface, resulting in the deletion of important medical information. Also, the engraved medical jewelry may not contain up to date information because updating the medical information would require the purchase of a new piece of jewelry. Another limitation of the medical alert jewelry is that they require the person to remember to wear the piece whenever they leave the home.

Other medical alert systems are inefficient in providing the medical information to emergency medical providers. One such system requires that the person carry a card containing personal information and a number to call to retrieve the medical information. This system is inefficient by requiring the medical response team to locate the card, contact the information provider using the telephone number on the card and wait for the information to be relayed to the medical provider. All of these actions waste valuable time when providing emergency medical care.

It is an object of this invention, therefore, to provide a system and method of communicating personal information to healthcare providers that overcomes the deficiencies and obstacles described above.

SUMMARY OF THE INVENTION

One aspect of the invention provides a system for providing medical information of a vehicle user to a medical provider using a wireless network. The system comprises a key device including stored medical information of a vehicle user, a telematics unit in communication with a vehicle data network, and a transient memory storage located within the vehicle and in communication with the key device and the vehicle data network. The system further includes a call center in wireless communication with the telematics unit via a wireless network. The stored medical information is transmitted from the transient storage of the vehicle via the vehicle data network to the telematics unit. Further, the medical information is transferable from the telematics unit to the call center via the wireless network.

Another aspect of the invention provides a method for providing medical information of a vehicle user to medical providers. The method comprises receiving vehicle user medical information in a key device, transmitting the medical information from the key device to a storage unit within a vehicle and transmitting the stored medical information from a telematics unit to a call center responsive to an emergency event.

Another aspect of the invention provides a system for providing medical information of a vehicle user to medical care providers. The system includes key device means for receiving and storing vehicle user medical information, vehicle storage means for receiving and storing medical information transmitted from the key device means and means for wirelessly transmitting the medical information from the vehicle storage means to a call center in response to an emergency event.

The aforementioned, and other features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims and equivalents thereof.

DETAILED DESCRIPTION OF THE PRESENTLY PREFERRED EMBODIMENTS

Figure 1:
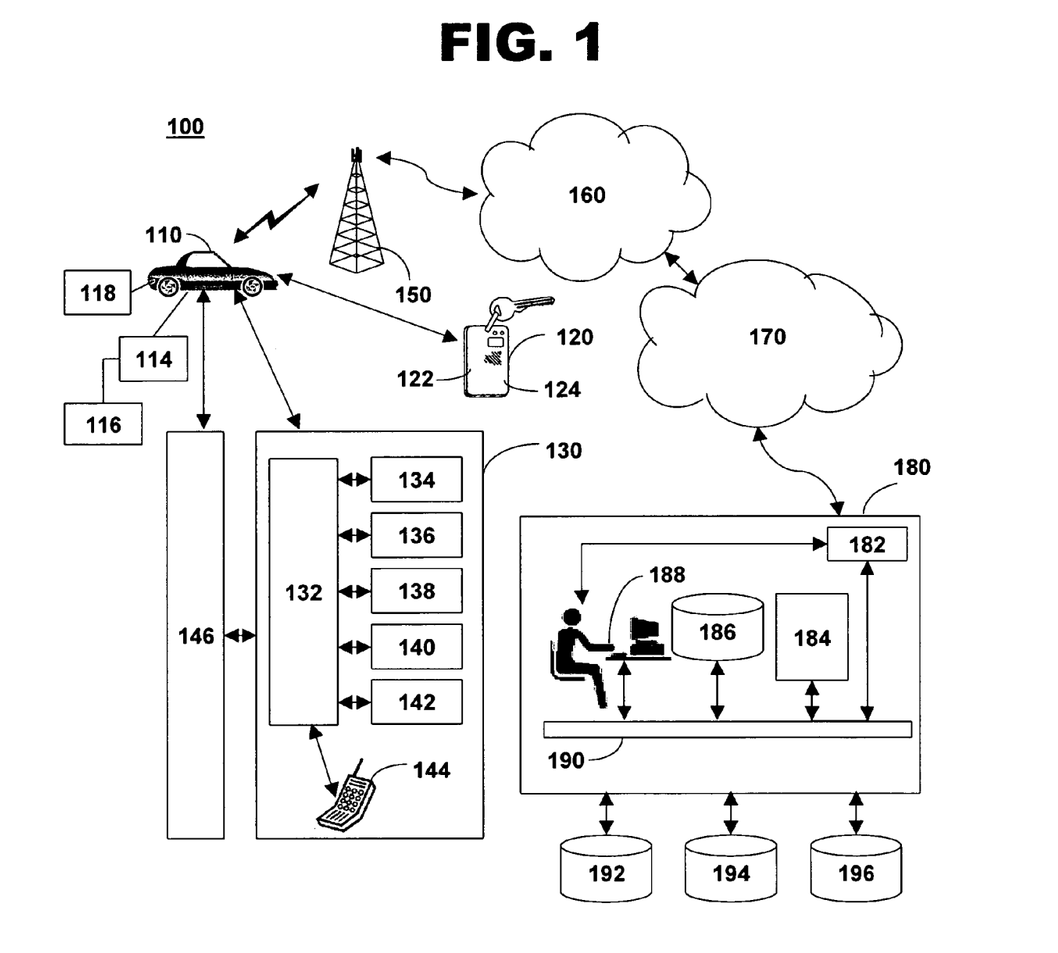
FIG. 1 shows an illustration of one embodiment of a system for maintaining and communicating personal information through a mobile vehicle using a wireless key device, in accordance with the present invention.

FIG. 1 shows an illustration of one embodiment of a system for maintaining and communicating personal information through a mobile vehicle using a wireless key device, in accordance with the present invention at 100. The wireless key system, also known as a personalized key system, is able to communicate with and transfer information to a database located within the vehicle while the keying device is in the ignition or is docked in the vehicle. Wireless key system 100 includes a mobile vehicle 110, a key device 120, a communications controller or telematics unit 130, one or more wireless carrier systems 150, one or more communication networks 160, one or more land networks 170, and one or more call centers 180. Mobile vehicle 110 is equipped with suitable hardware and software for transmitting and receiving voice and data communications.

Mobile vehicle 110 also includes ignition system 114, in-vehicle transient storage 118 and vehicle network 146. Ignition system 114 includes software monitor 116. Software monitor 116 retrieves the personal data stored in key device 120 and places the data in transient storage 118 of vehicle 110. Software monitor 116 also communicates the data placed in transient storage 118 to the telematics unit 130 via vehicle network 146. Software monitor 116 includes suitable hardware and software for transmitting and receiving data. In one embodiment, telematics unit 130 includes transient storage 118.

Mobile vehicle 110 also includes various types of sensors for detection of emergency events. In one embodiment, for example, the vehicle contains a sensor for detecting the deployment of the airbags. The vehicle may also include sensors that detect vehicle rollover that may occur during a traffic accident. Other sensors may detect damage to the vehicle body that may occur during an accident. These sensors may send analog or digital signals to the telematics unit 130 via vehicle network 146 upon the occurrence of the emergency event, such as, for example, the deployment of an air bag.

Key device 120 includes persistent storage memory 122 for storing personal data and a controller 124 for transmitting stored data to transient storage 118. In one embodiment, persistent storage memory 122 is located on a key fob that is in wireless communication with ignition system 114. In another embodiment, persistent storage memory 122 is located on a chip contained in the ignition key. In one embodiment, the personal data stored in persistent memory 122 comprises the medical history of the user. In another embodiment the personal data stored in persistent memory comprises an encrypted code. This encrypted code would be transmitted to medical care providers and used to gain access to medical records stored on a remotely located database 192, 194, 196.

Telematics unit 130 includes a digital signal processor (DSP) 132 connected to a wireless modem 134, a global positioning system (GPS) unit 136, an in-vehicle memory 138, a microphone 140, one or more speakers 142, and an embedded or in-vehicle mobile phone 144. DSP 132 may also be referred to as a microcontroller, controller, host processor, or vehicle communications processor. GPS unit 136 provides longitude and latitude coordinates of the vehicle. In-vehicle mobile phone 144 may be an analog, digital, dual-mode, dual-band, multi-mode or multi-band cellular phone.

DSP 132 executes various computer programs that control programming and operational modes of electronic and mechanical systems within mobile vehicle 110. DSP 132 controls communications between telematics unit 130, wireless carrier 150, and call center 180. A voice-recognition application may be installed in mobile vehicle 110 to translate human voice input through microphone 140 into digital signals. The voice-recognition application may be located in DSP 132 or other on-board electronic equipment such as a radio or electronic controller. DSP 132 may also generate and accept digital signals transmitted between key device 120 and telematics unit 130.

Mobile vehicle 110 via a vehicle communication network 146 sends signals to various pieces of equipment and systems within mobile vehicle 110 to perform various functions such as unlocking a door, opening the trunk, setting personal comfort settings, and calling from telematics unit 130.

Mobile vehicle 110 via telematics unit 130 sends and receives radio transmissions from wireless carrier system 150. Wireless carrier system 150 comprises any suitable system for transmitting a signal from mobile vehicle 110 to communication network 160.

Communication network 160 comprises services from one or more mobile telephone switching offices and wireless networks. Communication network 160 connects wireless carrier system 150 to land network 170. Communication network 160 comprises any suitable system or collection of systems for connecting wireless carrier system 150 to mobile vehicle 110 and land network 170.

Land network 170 may be a public-switched telephone network (PSTN) or, in another embodiment, an Internet protocol (IP) network. Land network 170 may be comprised of a wired network, an optical network, a fiber network, another wireless network, or any combination thereof. Land network 170 is connected to one or more landline telephones. Land network 170 connects communication network 160 to call center 180. Communication network 160 and land network 170 connects wireless carrier system 150 to a communication node or call center 180.

Call center 180 contains one or more voice and data switches 182, one or more communication services managers 184, one or more communication services databases 186, one or more communication services advisors 188, and one or more network systems 190.

Call center 180 provides a plurality of functions. Call center 180 comprises a location where many calls are received and serviced at the same time, or where many calls are sent at the same time. The call center 180 further comprises a telematics call center, facilitating communications to and from telematics unit 130 in mobile vehicle 110. The call center may be a voice call center, providing verbal communications between a live advisor in the call center and a subscriber in a mobile vehicle, a virtual call center having virtual advisors or a combination of both. The call center may contain each of these functions, and specifically, the call center 180 may operate using a combination of real and virtual advisors.

Call center 180 contains one or more voice and data switches 182. Switch 182 connects land network 170 to call center 180. Switch 182 transmits voice or data transmissions from call center 180. Switch 182 also receives voice or data transmissions from telematics unit 130 in mobile vehicle 110 through wireless carrier system 150, communication network 160, and land network 170. Switch 182 receives from or sends to one or more communication services managers 184 data transmissions via one or more networks 190.

Communication services manager 184 includes suitable hardware and software capable of providing requested communication services to telematics unit 130 in mobile vehicle 110. Communication services manager 184 sends data transmissions to or receives data transmissions from one or more communication services databases 186 and one or more communication services advisors 188 via network system 190. Communication services database 186 sends data transmissions to or receives data transmissions from communication services advisor 188 via network system 190. Communication services advisor 188 receives voice or data transmissions from or sends voice or data transmissions to switch 182.

Communication services manager 184 sends data transmissions to or receives data transmissions from one or more third party databases 192, 194,196.

Communication services manager 184 provides one or more of a variety of services, including enrollment services, navigation assistance, directory assistance, roadside assistance, business or residential assistance, information services assistance, emergency assistance, and communications assistance. Communication services manager 184 transmits data to telematics unit 130 in mobile vehicle 110 through wireless carrier system 150, communication network 160, land network 170, voice and data switch 182, and network 190. Communication services manager 184 may store or retrieve data and information from communication services database 186. Communication services manager 184 provides requested information to communication services advisor 188.

Communication services advisor 188 may be a real advisor or a virtual advisor. A real advisor is a human being in verbal communication with a user or subscriber in mobile vehicle 110 via telematics unit 130. A virtual advisor is a synthesized voice interface responding to requests from telematics unit 130 in mobile vehicle 110.

Communication services advisor 188 provides services to telematics unit 130 in mobile vehicle 110. Services provided by communication services advisor 188 may include enrollment services, navigation assistance, real-time traffic advisories, directory assistance, roadside assistance, business or residential assistance, information services assistance, emergency assistance, and communications assistance. Communication services advisor 188 may communicate with telematics unit 130 in mobile vehicle 110 through wireless carrier system 150, communication network 160, and land network 170 using voice transmissions, or through communication services manager 184 and switch 182 using data transmissions. Switch 182 may select between voice transmissions and data transmissions.

In communicating with telematics unit 130, key fob 120 may use wireless networking protocols such as IEEE 802.11b and IEEE 802.15 that operate in the 2.4-GHz industrial, scientific and medical (ISM) band. IEEE 802.11b, often referred to as wireless fidelity (Wi-Fi), is a standard commonly used for communication on wireless local area networks (WLAN). Key fob 120 may also use the lower-powered technology of Bluetooth™ or the IEEE 802.15 protocol, a short-range radio standard often employed in wireless personal area networks (WPAN). Bluetooth™ is particularly suited for wireless connections within 10 meters. WiFi and Bluetooth™ technology allow communication between devices located within approximately 10 to 100 meters of one another.

Figure 2:
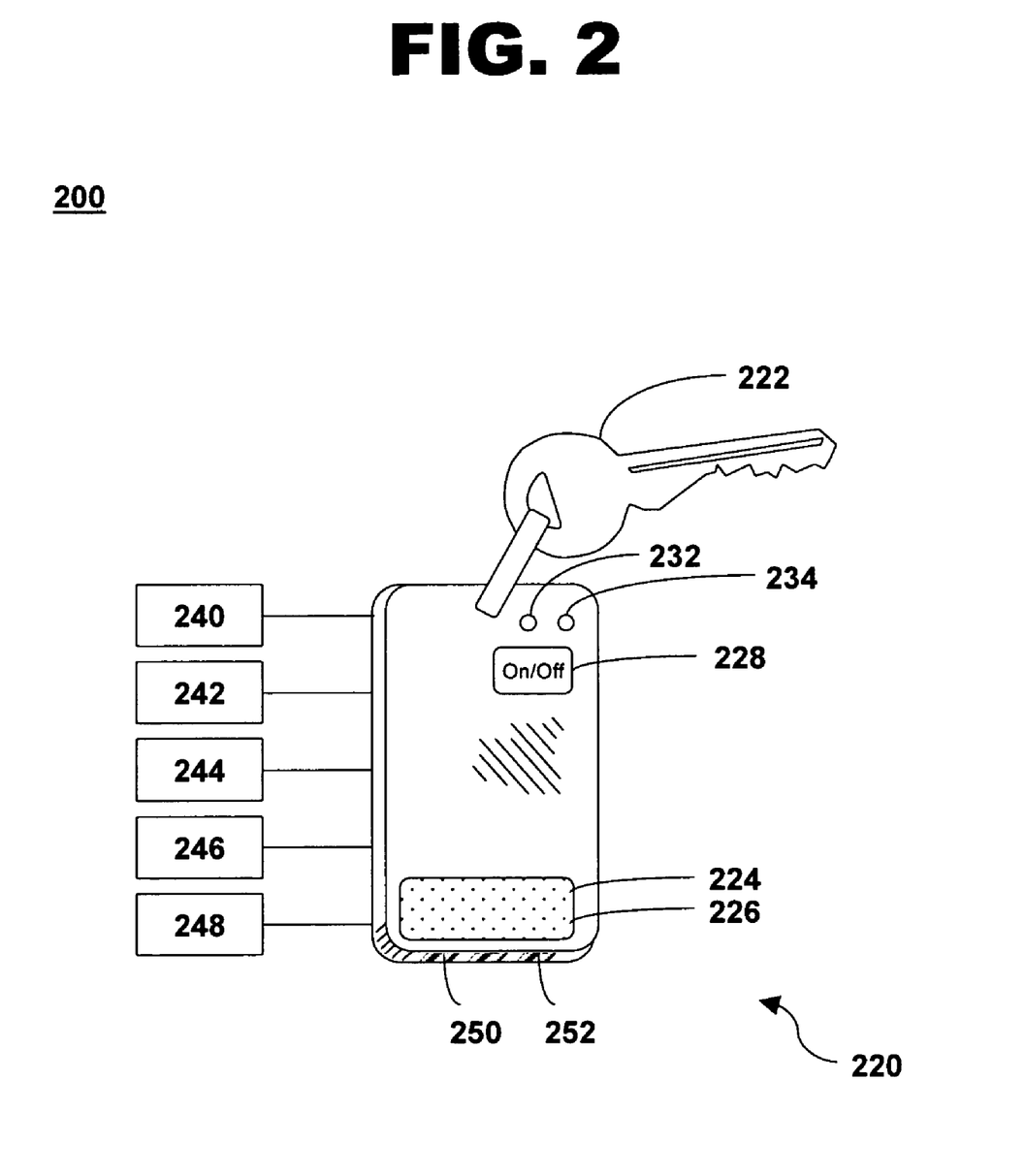
FIG. 2 illustrates one embodiment of a wireless key device for a mobile vehicle, in accordance with the current invention.

FIG. 2 is an illustration of one embodiment of a wireless key device for a mobile vehicle, in accordance with the present invention at 200. In this embodiment, key device 200 is a key fob 220. Key fob 220 is a small hardware device with a size and dimensions for comfortably fitting into a purse, on a belt, or in a pocket. The key fob may control basic services such as unlocking doors, as well as facilitate higher end services such as defining programmable steering wheel buttons, seat positions and radio stations.

In one embodiment, key fob 220 includes controller 240, persistent memory 242, transceiver 244, antenna 246 and battery 248. Key fob 220 also includes an on/off switch 228, an LED 232 such as a green LED, and LED 234 such as a red LED. Battery 248, may be a rechargeable battery, such as a lithium ion battery, that is recharged while the key fob is docked in a recharging device. Key fob 220 includes connector 250 that provides electrical connection to the battery charging docking mechanism. Key fob 220 also includes connector 252 to provide a connection to an external data source so that personal data may be transferred from the external data source to the persistent memory 242. Key fob 220 may also include a directional microphone 224 and a speaker 226.

Battery 248 provides power to run LEDs 232 and 234, controller 240, memory 242, and transceiver 244. LEDs may be used as power indicators, lighted green LED 232 meaning a charged battery and red LED 234 meaning a low-charged battery. In another embodiment, battery 248 also provides power to run microphone 224 and speaker 226. Key fob 220 may or may not be linked to one or more keys 222. Key fob 220 may have an intelligent key containing information about the owner and user preferences, such as favorite radio stations, personal calendar and business contact information.

Transceiver 244 may send analog or digital radio signals from the key fob 220 to transient storage of vehicle 110 via antenna 246. In one embodiment, data is transmitted to transceiver 244 of key fob 220 wirelessly via antenna 246 and stored in persistent memory 242.

The mobile vehicle may have several key fobs 220, one for each driver. Each key fob 220 would contain personal medical information stored in the persistent memory 242 specific to each driver. Additional stored information may include personal comfort settings such as seat position, temperature settings, mirror alignments, and radio-station preferences. In another embodiment, key fob 220 contains personal medical information for more than one driver.

Key fob 220 includes controller 240 with computer applications that are optimized to capture data transmitted to the key fob and to transmit data to transient storage of the vehicle. Other applications may control various other operations of key fob 220.

Associated with controller 240 is a persistent memory 242 such as a solid-state flash memory chip along with volatile memory. Memory 242 stores the personal medical records and other personal data of the driver that are transmitted to transient storage of the vehicle when the ignition system is activated at start-up. In another embodiment, persistent memory 242 stores an encryption code unique to the driver instead of the driver's medical history. Memory 242 may also store user preferences or personalized settings.

Besides communicating to the transient storage of vehicle 110 through wireless transmissions, key fob 220 can make a wired hookup via connector 252 making electrical and mechanical contact with an outside data source. The key fob 220 may be connected to a computer to download the driver's medical information from a medical provider database.

Those with skill in the art will recognize that key fob may include other embodiments and features not depicted. For example, in another embodiment, the key fob includes personal medical information for at least two individuals. For this embodiment the key fob is able to distinguish between the different drivers in order to send the appropriate data if required. This embodiment includes a biometric sensor that can distinguish one driver from another. In one such embodiment, the biometric sensor is a fingerprint sensor, as are well known in the art. In this embodiment, the driver's fingerprint is stored in the persistent memory of the key fob and is correlated to the driver's personal medical information or personal encryption code. The controller would then send the identified driver's medical information or encryption code to the transient storage of the telematics unit.

In another embodiment, the biometric sensor comprises speech recognition software and hardware as is known in the art. In this embodiment, the speech of one driver is identified and correlated to speech data stored in the key fob memory.

Once the speech is identified it is correlated to that specific driver's personal medical information or encryption code.

Figure 3:
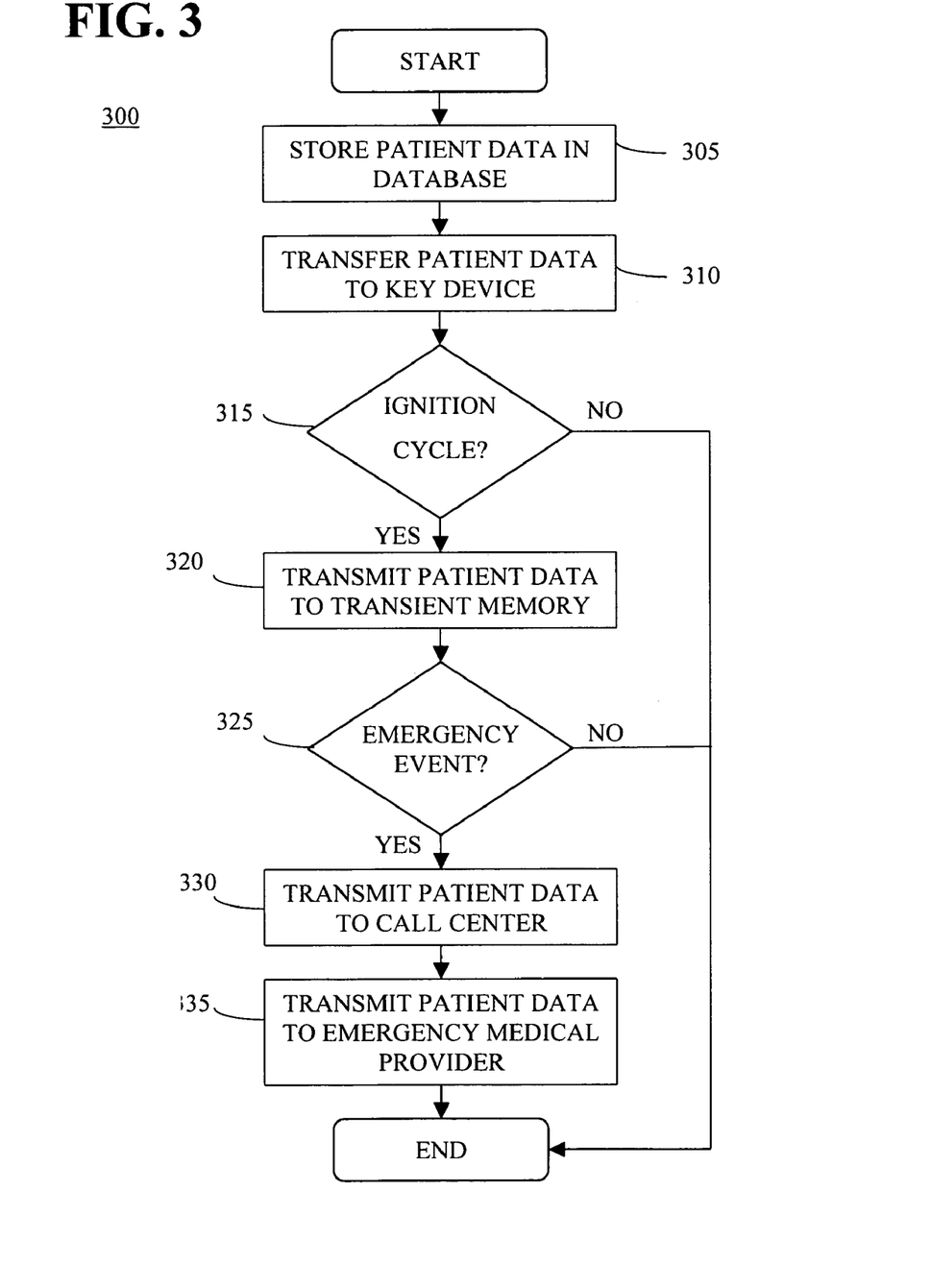
FIG. 3 is a flow diagram of one embodiment of a method for maintaining and communicating personal information through a mobile vehicle using a wireless key device, in accordance with the current invention.

FIG. 3 is a flow diagram of one embodiment of a method for communicating personal medical information from a mobile vehicle to emergency medical providers using a wireless communications system, and is shown generally at 300. The method utilizes the system illustrated and described above in relation to FIGS. 1 and 2. The key fob includes a controller and persistent memory. The key fob is also equipped with a transceiver for wireless communications using a local short range wireless network. Wireless communications are transmitted and received using any suitable analog or digital communications technologies. The wireless communications between the key fob and the in-vehicle transient storage may be executed in accordance with a wireless communication protocol such as the IEEE 802.11 standards.

One embodiment of a method for communicating personal medical information between a mobile vehicle and a medical provider begins with storing patient data belonging to service subscriber on a database (Block 305). This database may be located at the service subscriber's doctor's office or hospital and may be stored on a personal computer as is well known in the art. The stored data is then transferred to the subscriber's key fob (Block 310). In one embodiment, the patient medical data is transferred from the database to the key fob using a wired connection between the personal computer and the key fob connector 252. In another embodiment, the patient medical data is transferred from the personal computer to the key fob using a local short range wireless network.

Once the personal medical data has been stored on the key fob the service subscriber uses the key fob in a normal manner when used with the vehicle 110 that is part of system 100 illustrated in FIG. 1. For example, the user may use the key fob to lock or unlock the vehicle doors or activate a vehicle alarm. If the key is used the controller within the key fob determines whether an ignition cycle has been activated (Block 315). If an ignition sequence has not been initiated the method ends. If it is determined that an ignition cycle has began, the controller 240 of key fob 220 transmits the subscriber medical records to the in-vehicle transient storage 118 (Block 320). The medical data is transmitted to the in-vehicle transient storage using the local short range wireless network. Those with skill in the art will recognize that there are other methods of transmitting data from the key fob persistent storage to the in-vehicle transient storage. For example, the transmission may result from physical or electric communication between the persistent storage and the transient storage. In another example, the transmission may result from a Hall effect sensor, as is well known to those of ordinary skill in art, or may result from other magnetic sensors.

The personal medical information transmitted to in-vehicle transient storage is temporarily stored in the transient memory. In one embodiment, the medical information is kept in transient memory as long as the vehicle is operating. In another embodiment, the medical information is kept in transient storage for a predetermined length of time after the vehicle is turned off. In one embodiment, for example, the information is kept in transient storage for ten minutes after the vehicle is turned off. In another example, the information is kept in storage for thirty minutes post engine shut off.

During the operation of the vehicle an emergency event may occur (Block 325). The emergency event may be a vehicle accident that may result in damage to the vehicle. The vehicular emergency event may be detected by sensors placed within the vehicle, such as, airbag deployment sensors or other sensors that detect damage to the vehicle such as those placed on front and rear bumpers or in crumple zones of the vehicle body. The sensor would send a signal to the vehicle telematics unit 130 of vehicle 110 via vehicle network 146 that an emergency event has occurred. Telematics unit 130 would then transmit an emergency call to the call center 180 and at the same time transmit the medical information to the call center (Block 330). In one embodiment, the transmission of the emergency call to the call center may be initiated by a voice prompt from the telematics unit requesting instructions from the vehicle driver. For example, upon receiving an emergency event signal, the telematics unit may ask "Send emergency request?" to which the driver may say "Yes" or "No". If the driver says "Yes" the emergency call is transmitted, if the driver says "No" the method terminates. In another embodiment, if no verbal response is received from the driver, the emergency call is transmitted along with the personal medical data.

The call center would then transmit the received personal medical data to the appropriate emergency response personnel, such as, for example, emergency medical technicians and paramedics. Alternatively, the information may be transmitted to a public safety answering point (PSAP) (i.e. a 911 call center) that will then send the information to the appropriate emergency response personnel.

However, in some circumstances the emergency event (Block 325) may not involve the vehicle but instead may only involve the driver. For example, the driver's health may be in jeopardy such as when the driver experiences a sudden onset of an illness or a heart attack. In these situations the vehicle driver may initiate the transmission of information by pressing a button operably connected to the telematics unit 130. In one embodiment, telematics unit 130 includes an emergency button that, when depressed transmits a request for emergency assistance. In another embodiment, the emergency request may be voice activated. Once the emergency request has been initiated, the telematics unit 130 transmits the personal medical information located in transient storage 118 along with the request for emergency assistance (Block 330). The call center will then transmit the personal medical information to the appropriate personal as discussed above (Block 335).

Figure 4:
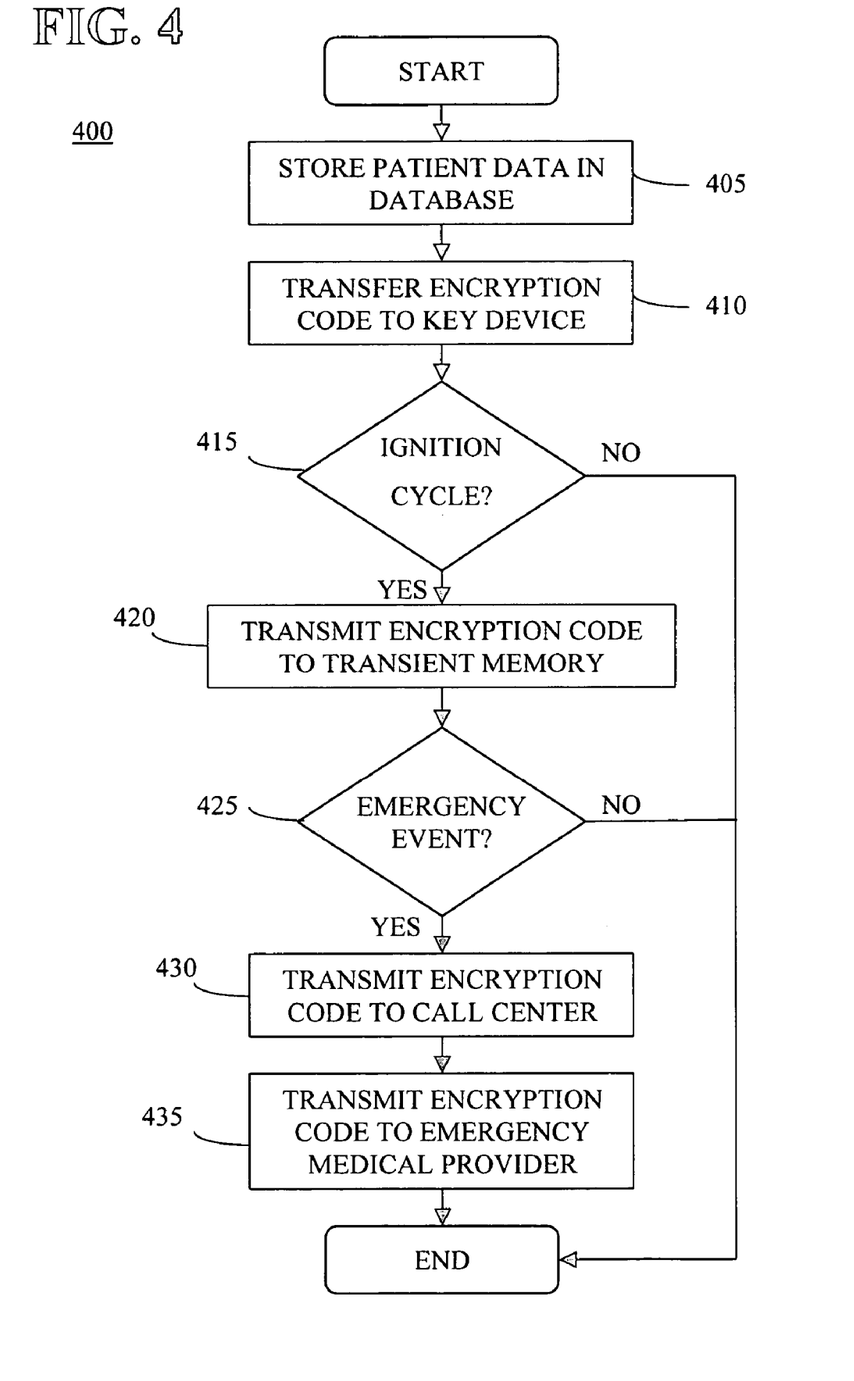
FIG. 4 is a flow diagram of another embodiment of a method for maintaining and communicating personal information through a mobile vehicle using a wireless key device, in accordance with the current invention.

FIG. 4 is a flow diagram of another embodiment of a method for communicating personal medical information from a mobile vehicle to emergency medical providers using a wireless communications system, and is shown generally at 400. The method utilizes the system illustrated and described above in relation to FIGS. 1 and 2. The key fob includes a controller and persistent memory. The key fob is also equipped with a transceiver for wireless communications using a local short range wireless network. Wireless communications are transmitted and received using any suitable analog or digital communications technologies. The wireless communications between the key fob and the in-vehicle transient storage may be executed in accordance with a wireless communication protocol such as the IEEE 802.11 standards.

One embodiment of a method for communicating personal medical information between a mobile vehicle and a medical provider begins with storing patient data belonging to service subscriber on a database (Block 405). This database 192, 194, 196 may be located at the service subscriber's doctor's office or hospital or may be located at a third party data repository. The personal medical records stored in the database would be associated with a unique encryption code. The encryption code can be used to gain access to specific patient records.

The encryption code is then transferred to and stored on the subscriber's key fob (Block 410). In one embodiment, the encryption code is transferred from the database to the key fob using a wired connection between the computer housing the database and the key fob connector 252. In another embodiment, the encryption code is transferred from the database housing the encryption code to the key fob using a local short range wireless network.

Once the encryption code has been stored on the key fob the service subscriber uses the key fob in a normal manner when used with the vehicle 110 that is part of system 100 illustrated in FIG. 1. For example, the user may use the key fob to lock or unlock the vehicle doors or activate a vehicle alarm. If the key is used the controller within the key fob determines whether an ignition cycle has been activated (Block 415). If an ignition sequence has not been initiated the method ends. If it is determined that an ignition cycle has began, the controller 240 of key fob 220 transmits the subscriber encryption code to the in-vehicle transient storage 118 (Block 420). The encryption code is transmitted to the in-vehicle transient storage using the local short range wireless network. Those with skill in the art will recognize that there are other methods of transmitting data from the key fob persistent storage to the in-vehicle transient storage.

The encryption code transmitted to in-vehicle transient storage is temporarily stored in the transient memory. In one embodiment, the encryption code is kept in transient memory as long as the vehicle is operating. In another embodiment, the encryption code is kept in transient storage for a predetermined length of time after the vehicle is turned off. In one embodiment, for example, the encryption code is kept in transient storage for ten minutes after the vehicle is turned off. In another example, the encryption code is kept in storage for thirty minutes post engine shut off.

During the operation of the vehicle an emergency event may occur (Block 425). The emergency event may be a vehicle accident that may result in damage to the vehicle. The vehicular emergency event may be detected by sensors placed within the vehicle, such as, airbag deployment sensors or other sensors that detect damage to the vehicle such as those placed on front and rear bumpers or in crumple zones of the vehicle body. The sensor would send a signal to the vehicle telematics unit 130 of vehicle 110 via vehicle network 146 that an emergency event has occurred. Telematics unit 130 would then transmit an emergency call to the call center 180 and at the same time transmit the encryption code to the call center (Block 430).

The call center would then transmit the encryption code to the appropriate emergency response personnel, such as, for example, emergency medical technicians and paramedics. Alternatively, the information may be transmitted to a public safety answering point (PSAP) (i.e. a 911 call center) that will then send the encryption code to the appropriate emergency response personnel.

However, in some circumstances the emergency event (Block 425) may not involve the vehicle but instead may only involve the driver. For example, the driver's health may be in jeopardy such as when the driver experiences a sudden onset of an illness or a heart attack. In these situations the vehicle driver may initiate the transmission of encryption code by pressing a button operably connected to the telematics unit 130. In one embodiment, telematics unit 130 includes an emergency button that, when depressed transmits a request for emergency assistance. In another embodiment, the emergency request may be voice activated. Once the emergency request has been initiated, the telematics unit 130 transmits the encryption code located in transient storage 118 along with the request for emergency assistance (Block 430). The call center will then transmit the encryption code to the appropriate personal as discussed above (Block 435).

The emergency medical providers would then use the encryption code to access the medical information for the service subscriber. This may be done in route to the vehicle of the service subscriber or it may be done at the scene of the accident or, alternatively, the information may be accessed at the hospital once the service subscriber arrives.

In another embodiment of the system for communicating medical information from a vehicle to the medical provider the key device comprises a key with an embedded microchip. Keys having microchips are known in the art for use as a theft deterrent. In this embodiment the embedded chip has persistent memory sufficient for storing either the medical information or the encryption code. The medical information or encryption code would be transferred to transient memory upon starting the vehicle.

In still another embodiment, the key device is similar to a credit card, the card having the medical information or encryption code stored on the card. When the card is used to start the vehicle, the medical information or encryption code would be transferred to transient storage.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A system for providing medical information of a vehicle user, comprising:
    a key device corresponding to a particular vehicle, the key device having stored therein an encryption code associated with the medical records; of the vehicle user;
    a transient memory storage located within the particular vehicle and in communication with the key device, the transient memory storage configured to i) receive a transmission of the encryption code from the key device prior to an emergency event, and ii) temporarily store the encryption code prior to the emergency event;
    a telematics unit in communication with the transient memory storage device and configured to receive a transmission of the encryption code from the transient memory storage in response to the emergency event involving the particular vehicle; and
    a call center in wireless communication with the telematics unit via a wireless network, wherein the call center is configured to i) receive a transmission of the encryption code from the telematics unit in response to the emergency event, and ii) transfer the received encryption code to emergency personnel.

2. The system of claim 1 wherein the transient memory storage is in communication with the key device via a vehicle data network, and wherein the vehicle data network is a local short range wireless network.

3. The system of claim 1 wherein the key device comprises a key fob, the key fob including:
    a controller for receiving the encryption code and storing the encryption code in a persistent memory; and
    a transceiver for sending the stored encryption code to the transient memory storage located in the vehicle.

4. The system of claim 3, further comprising:
    a biometric sensor located on the key fob and operably connected to the controller, the biometric sensor for sensing biometric data of at least one vehicle user.

5. The system of claim 1, further comprising:
    a plurality of sensors for detecting damage to the particular vehicle during the emergency event, the plurality of sensors operably connected to the telematics unit, wherein when the emergency event occurs, at least one of the plurality of sensors sends a signal to the telematics unit indicating that the emergency event has occurred.

6. The system of claim 1 wherein the key device comprises a key including an embedded microchip having a persistent memory storage for storing the encryption code.

7. The system of claim 1, further comprising a database including the medical records; of the vehicle user.

8. A method for providing medical records; of a vehicle user, the method comprising:
    storing an encryption code in a key device corresponding to a particular vehicle, the encryption code associated with the medical information stored in a database;
    transmitting the encryption code from the key device to a vehicle storage unit of the particular vehicle and temporarily storing the transmitted encryption code in the vehicle storage unit prior to an emergency event;
    transmitting, from the vehicle storage unit to an in-vehicle telematics unit of the particular vehicle and from the in-vehicle telematics unit to a call center, the temporarily stored encryption code in response to the emergency event involving the particular vehicle;
    transmitting the encryption code from the call center to an emergency personnel; and
    accessing, via the emergency personnel, the medical information from the database using the encryption code.

9. The method of claim 8 wherein prior to storing the encryption code in the key device, the method further comprises:
    associating the encryption code with the medical records; of the vehicle user;
    storing the encryption code in the database; and
    transferring the encryption code from the database to the key device.

10. The method of claim 9 wherein the transferring of the encryption code from the database to the key device is accomplished using a local short range wireless network or a wired connection.

11. The method of claim 8 wherein after storing the encryption code in the key device, the method further comprises initiating an ignition cycle of the vehicle.

12. The method of claim 11 wherein upon the initiating of the ignition cycle of the particular vehicle, the method further comprises transmitting the encryption code from the key device to the vehicle storage unit.

13. The method of claim 8 wherein the encryption code is temporarily stored in the vehicle storage unit i) while a vehicle ignition is operating; or ii) for a predetermined amount of time after the vehicle ignition is turned off.

14. A system for providing medical records; of a vehicle user, comprising:
    key device means corresponding to a particular vehicle for receiving and storing an encryption code, the encryption code associated with the medical information of the vehicle user stored in a database;
    vehicle storage means of the particular vehicle for i) receiving a transmission of the encryption code from the key device means prior to an emergency event, and ii) temporarily storing the encryption code prior to the emergency event;
    an in-vehicle telematics unit of the particular vehicle in communication with the vehicle storage means;
    means for transmitting i) from the vehicle storage means to the in-vehicle telematics unit, and ii) from the in-vehicle telematics unit to a call center, the temporarily stored encryption code in response to the emergency event involving the particular vehicle; and
    means for accessing, via the emergency personnel, the medical information from the database using the encryption code.

15. The system of claim 14, further comprising:
    means for sensing biometric data of at least one vehicle user, the biometric sensing means located on the key device means; and
    means for correlating the sensed biometric data to the medical records; of the at least one vehicle user.

\* \* \* \* \*